United States Patent [19]
Facciotti

[11] Patent Number: 5,565,346
[45] Date of Patent: Oct. 15, 1996

[54] TRANSFORMATION AND REGENERATION SYSTEM FOR LEGUMES

[75] Inventor: Daniel Facciotti, Davis, Calif.

[73] Assignee: Calgene, Inc., Davis, Calif.

[21] Appl. No.: 225,332

[22] Filed: Jul. 27, 1988

[51] Int. Cl.$^6$ .............................. C12N 15/82; C12N 5/14; A01H 4/00
[52] U.S. Cl. ............... 435/172.3; 800/205; 800/DIG. 26
[58] Field of Search .................................. 935/53, 55, 67; 435/172.1, 240.4, 240.45, 240.46, 240.48, 240.49, 172.3; 800/205, DIG. 23-26

[56] References Cited

U.S. PATENT DOCUMENTS

| | | | |
|---|---|---|---|
| 4,672,035 | 6/1987 | Daridonis et al. | 435/240.5 |
| 5,015,580 | 5/1991 | Christou et al. | 435/172.3 |

OTHER PUBLICATIONS

Lippmann and Lippman, "Induction of somatic embryos in cotyledonary tissue of soybean, *Glycine max* L. Meer", *Plant Cell Reports* (1984) 3:215–218.
Klee and Rogers, "Plant Gene Vectors and Genetic Transformation: Plant Transformation Systems Based on the Use of *Agrobacterium tumefaciens*", *Cell Culture and Somatic Cell Genetics of Plants* (1989) vol. 6, pp. 1–23.
Johnston et al., (1988) Science, 240:1538–1541.
Boynton et al., (1988) Science, 240:1534–1538.
Klein et al., (1988) Bio/Technology 6:559–563.
Christou, et al., Plant Physiol., 87:671–674 (1988).
Charest, et al., Theor. Appl. Genet., 75:438–445 (1988).
Jefferson et al., The Embo Journal, 6:3901–3907 (1987).
Jefferson, Richard A., Plant Molecular Bilogy Report, 5:387–405 (1987).
Van et al., Biotechnology in Agriculture and Forestry, 2:556–567 (1986).
Kamate et al., Canadian J. Botany, 59:775–781 (1981).
Kyozuka, et al. (1987) Mol. Gen. Genet. 206:408–413.
Lazzeri, et al. (1985) Plant Molecular Biology Reporter 3:160–167.
Ghazi, et al. (1986) Plant Cell Reports 5:452–456.
Klein, et al. (1987) Nature 327:70–73.
Jordan et al (1988) Plant Cell Reports 7:285–287.
Larkin et al (1988) Plant Science 58:203–210.

*Primary Examiner*—Che S. Chereskin

[57] ABSTRACT

Novel methods and compositions are provided for regenerating untransformed or transgenic leguminous plants from thin layer explants of immature embryonic cotyledons. Transgenic plants are preferably obtained by bombarding the thin layer explants at high velocity with DNA expression cassettes adsorbed to tungsten particles.

6 Claims, 3 Drawing Sheets

TRANSFORMATION AND REGENERATION SYSTEM FOR LEGUMES

TECHNICAL FIELD

The field concerns methods and compositions for modulating genotypes and related phenotypes of leguminous dicotyledons by means of bombardment with DNA constructs adsorbed to metallic particles.

BACKGROUND

While the ability to manipulate bacterial and mammalian cells by hybrid DNA technology has been available for almost a decade, it was only in 1983 that the first successful expression of an exogenous gene in a plant cell was achieved. Lack of success in transforming plant cells was due at least in part to a lack of suitable vectors and methods for regenerating plants from transformed cells. A vector which has been used with significant success for transformation of plant species has been Agrobacterium. To date, dicotyledenous species, particularly petunia, tomato and tobacco have been the primary plant materials used in Agrobacterium transformation studies. The procedures for regeneration from somatic cells as well as for transformation are well established for these species. However, for some of the world's major agricultural crops, such as legumes, genetic engineering has been less successful either because of poor regenerability and/or transformation by Agrobacterium.

It would be of interest to develop more efficacious methods for transforming legumious plant cells outside the normal host range of Agrobacterium and to regenerate plants from transformed somatic cells.

Relevant Literature

Thin epidermal layers from hypocotils, stems, and pedicels, have been used for morphological studies in various plants such as tobacco, rapeseed, and winged bean. See for example Van et. al. *Biotechnology in Agriculture and Forestry.* (1986) 2:556–567 and Kamate et. al. *Canadian J. Botany* (1981) 59:775–781. Charest et. al. *Theor. Appl. Genet* (1988) 75:438–445 disclosed the use of thin layer explants for rapeseed transformation mediated by Agrobacterium. Transgenic plants were generated from the transformed thin layer explants.

SUMMARY OF THE INVENTION

Novel methods and compositions are provided for regeneration of leguminous plants as well as transformation of leguminous plant tissue and generation of transgenic plants. Thin layers of totipotent epidermal cells are prepared from cotyledons of immature embryos. The thin layers may be used directly for plant regeneration or may be transformed with a DNA construct comprising nucleic acid capable of replication in the host plant. Preferred techniques of the invention for obtaining transformed leguminous plants include bombardment of the thin layer with DNA constructs adsorbed to high density metallic particles. Plants can be generated, either before or after transformation, from the thin layers by culture in solid medium through the plantlet stage. The methods are effective for generating transgenic leguminous dicotyledons.

DESCRIPTION OF THE SPECIFIC EMBODIMENTS

Figure 1:
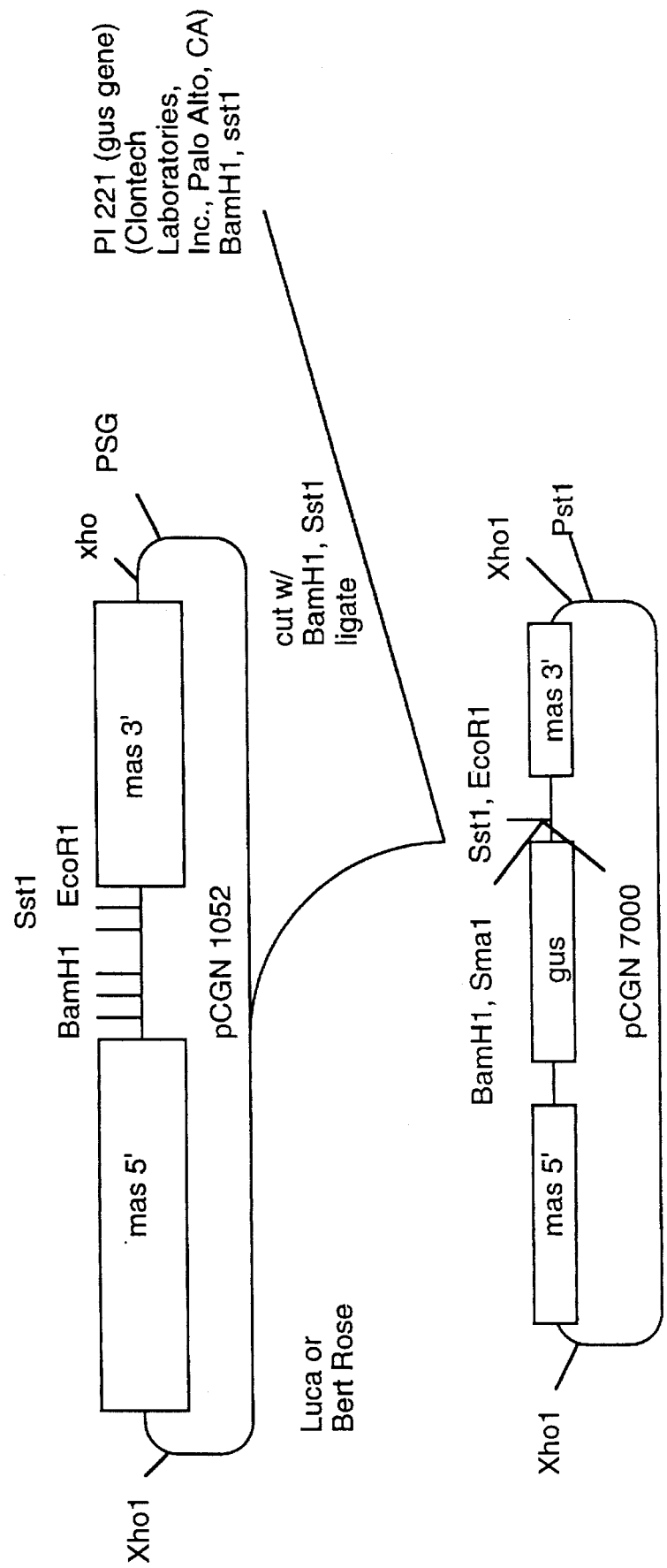
FIG. 1 shows the construction of the plasmid pCGN7000.

Novel methods and DNA constructs are provided for generating untransformed or transgenic leguminous plants from totipotent epidermal cells. Leguminous host cells are rendered more accessible to transformation and/or regeneration by preparing thin epidermal layers from cotyledons of immature embryos or from primary meristem tissue following preincubation of the donor tissue in nutrient medium. The thin layer explants can then be used directly for generation of a plant. Plants so obtained are capable of setting flowers and fruit.

The thin layer explants can also be used for obtaining transgenic plants. The thin layer explants are transformed using any of a variety of methods. A preferred method of transformation is to adsorb the DNA construct comprising nucleic acid capable of replication in the host cells to a metallic particle. The thin layer explant is then placed under vacuum and bombarded at least once at high velocity with the particles comprising the DNA construct. Plants are generated by culturing the thin layer explants, transformed or untransformed, in a series of gelified media until plantlets form. The plantlets are then transferred to soil for further growth.

The subject methods employ cells which possess totipotency and from which an entire plant can be generated. Examples of such cells are those obtainable from cotyledon epidermal tissue dissected from immature embryo and primary meristem tissue from a plant. By way of example, for preparing thin layer epidermal explants from immature cotyledon tissue, seeds are isolated and the part containing the embryo axis, the cotyledonary shoots and approximately 25% of the proximal end of the cotyledons is dissected and discarded. The remaining cotyledonary fragments maintained within the seed teguments are retained and preincubated on nutrient medium for about 18 to 24 hours prior to preparation of thin slices of cotyledon tissue. After the preincubation period, the cotyledonary fragments are separated from the teguments and thin slices are dissected from the adaxial side of each cotyledonary fragment. The slices are preferably about 2 to 5 mm long and approximately 1–3 mm wide, and include the epidermis and about 1 to 4 layers of subepidermal mesophyll cells.

For generation of a plant from the thin layer explant, whether or not it has been transformed, the explant tissue is initially encased in gelified nutrient medium, usually about 1 mm thick. This procedure is to protect and improve the survival rate of the explants. The encased explant is maintained at the proper temperature, with an appropriate photoperiod, to provide for development of embryoids in the explants. Any conventional nutrient medium may be employed for example, CM 3/0 medium gelified with Phytagar (Difco) 0.7% (Phillips and Collins, *Crop Sci.* (1979) 19:59–64). The period of time for development of an embryoid will be from about 10–15 days. During the following four weeks, embryoids will emerge from the gelified medium and can be transferred separately or attached to the cotyledonary mother tissue to a solid medium, CM 1/0 gelified with Phytagar, 0.7%. When the embryoids have formed roots, the plantlets may then be potted in a sand potting mix such as a mixture of peatmoss, vermiculite and sand, and permitted to grow.

If it is desired to transform the explant, any of a variety of methods can be used to introduce nucleic acid, capable of replication in the intended host plant, into a cell of the host plant. Methods include insertion into a tumor- or gall-producing plasmid, as naked DNA, or as an insertion in a plant DNA virus. In accordance with the subject invention, constructs and methods are provided which may be used to transform cells from virtually any higher plant. In particular the constructs and methods are useful for transformation of valuable economic crops such as legumes, in particular, soybean. The methods employ high velocity bombardment of the tissue explants with expression cassettes adsorbed to high density metal particles.

In preparing the expression cassette, the various DNA sequences may normally be inserted or substituted into a bacterial plasmid. Any convenient plasmid may be employed, which will be characterized by having a bacterial replication system, a marker which allows for selection in the bacterium, and generally one or more unique, conveniently located restriction sites. These plasmids, referred to as vectors, may include such vectors as pACYC184, pACYC177, pBR322, pUC9, the particular plasmid being chosen based on the nature of the markers, the availability of convenient restriction sites, copy number, and the like. One then defines a strategy which allows for the stepwise combination of the different fragments. As necessary, the fragments may be modified by employing synthetic adapters, adding linkers, employing in vitro mutagenesis or primer repair to introduce specific changes in the sequence, which may allow for the introduction of a desired restriction site, for removing superfluous base pairs, or the like. By appropriate strategies, one desires to minimize the number of manipulations required as well as the degree of selection required at each stage of manipulation. After each manipulation, the vector containing the manipulated DNA may be cloned, the clones containing the desired sequence isolated, and the vector isolated and purified. As appropriate, hybridization, restriction mapping or sequencing may be employed at each stage to ensure the integrity and correctness of the sequence.

The expression cassette will for the most part have the following formula:

P—S.G.—Te wherein:

P comprises a promoter region functional in a plant host, which promoter region may include promoters derived from Ti- or Ri-plasmids, such as the octopine synthase or nopaline synthase promoters; viral promoters such as the cauliflower mosaic virus 35S promoter (CaMV35S); plant promoters, particularly leguminous and plant host promoters of various structural genes, e.g., RuBP-carboxylase, more particularly SSU;

S.G. comprises a structural gene having an open reading frame and having at its 5'-end an initiation codon and at its 3'-end one or more nonsense codons; and Te intends a termination region functional in the plant host cell. The termination region may be derived from the 3'-region of the gene from which the initiation region was obtained or from a different gene. The termination region may be derived from a plant gene, particularly the tobacco ribulose biphosphate carboxylase small subunit termination region; the gene associated with the Ti plasmid such as the octopine synthase termination region; or the tml termination region.

A preferred promoter region is the CaMV 35S promoter. Another promoter of interest is the soybean small subunit promoter. The nucleotide sequence of the small subunit gene is described by Berry-Lowe, *J. Mol. Appl. Gen.* (1982) 1:483:498. A DdeI digest of a plasmid containing a genomic fragment which includes the SSU soybean gene yields a 1.1 kb 5' piece that can be used as a promoter fragment.

By use of the soybean SSU promoter, expression of the structural gene under transcriptional control of the SSU promoter can be light-induced. Thus, the expression of the gene is regulatable, where enhanced expression occurs during irradiation with light, while substantially reduced expression or no expression occurs in the absence of light.

By virtue of having a regulatable promoter in the soybean plant, one can provide for protection against herbicides, by providing a herbicide-resistant gene to be under the regulatable control of the SSU promoter. For example, by employing a mutated aroA gene, the enzyme 5-enolpyruvyl-3-phosphoshikimate synthase which is glyphosate-resistant can be produced under light induction. Thus, the soybean plant may be protected from glyphosate, allowing for the killing of weeds employing the glyphosate herbicide.

The promoter region will normally include a region for binding of RNA polymerase, as well as a cap site. In addition, there may be present enhancers, operators, activators, or other regions involved with transcriptional regulation. The terminator regions, besides including at least one terminating sequence, may also include a polyA signal.

The structural gene of interest may be any gene, either native, mutant native, or foreign to the plant host. By foreign is intended a gene not naturally found in the host cell. For native and mutant native genes, the gene may provide for increased capability of protein storage, improved nutrient source, enhanced response to light, enhanced dehydration resistance, e.g., to heat, salinity or osmotic pressure, herbicide resistance, e.g., glyphosate, or the like. Foreign genes may include enhancement of native capabilities, herbicide resistance, resistance to various pests, such as viruses, insects, bacteria or fungi, production of foreign products, as a result of expression of one or more foreign genes, or the like.

In many instances, it will be desirable to have at least one additional structural gene to serve as a marker associated with the expression cassette. Those plant cells in which the foreign gene has been stably introduced can be detected by means of the marker gene. For the most part, these expression cassettes will have the following formula:

$(P^1$—$(S.G.)^1$—$Te^1)$—$(p^2$—$(S.G.)^2$—$Te^2)$ wherein:

all of the symbols have the same functional definition as above, except that the superscripts for P and Te intend that the promoter and terminator regions may be the same or different and that the structural genes are different, where one is a marker and the other is a stuctural gene of interest. Of course, one may provide for a string of expression constructs having a plurality of the same or different genes in the construct. Thus, the presence of only two genes is merely illustrative.

As markers for structural genes, one can employ antibiotic resistance genes, e.g., a Bromoxynil resistance gene, a kanamycin resistance gene or methotrexate resistance gene (DHFR). Other markers can include the gus gene which encodes β-glucuronidase.

For use in the bombardment transformation technique, an expression cassette is adsorbed to a bombardment particle, typically consisting of tungsten having a diameter of about 0.5 μm to 3 μm with an average sized particle having a diameter of approximately 1.2 μm. Particles consisting of other metals having a density similar to tungsten may also find use, such as gold, platinum and the like. Typically, about 2.5 to 20 μg of DNA is adsorbed per 25 mg of bombardment particles. Any method to fix the DNA to the outside surface of the metal bombardment particles is acceptable, for example, the DNA may be air-dried onto the surface or precipitated out of solution onto the particles. The DNA must be secured to the particles for delivery, but not fixed in such a manner as to impede release of the DNA into the cell.

For transformation, approximately 0.8 to 1.2 μg of bombardment particles, to which the expression cassette has been adsorbed, is loaded into a particle gun (such as that available from Bolistics, Inc., Geneva, N.Y.) according to the manufacturer's directions. The thin layer explants are transferred to the bombardment chamber of the particle gun, and placed under vacuum of about 25 inches of mercury. The vacuum is then adjusted to approximately 29 inches of mercury, and the firing mechanism of the particle gun activated. The explant is bombarded at least once, preferably more than once, most preferably at least twice. The vacuum is then released, and the bombarded tissue gently embedded in gelified nutrient medium for generation of a transgenic plant. The methods used for generation of a transgenic plant are as described above for regeneration of a plant from an untransformed thin layer explant.

The presence of the desired gene in the plant itself can be established in a wide variety of ways, depending upon the nature of the gene. The presence of a gene which produces an exogenous product may be detected by isolation and lysis of the plant cell and an analysis of the cytoplasm for the exogenous product, or of the nucleus for the exogenous gene. The exogenous product may be detected by electrophoresis, chromotography, immunoassay, or the like. The gene can be dectected easily by hybridization, for example, by using Southern Blotting. Once a plantlet or plant has been shown to have been transformed, the cells of the plant may then be used repeatedly for tissue culture, followed by the growth of plantlets. Thus the modified plant can be repetitively regenerated by use of cell and tissue culture. In some instances, propagation may be maintained from seed, although monitoring for loss of the exogenous gene would be advisable.

The following examples are offered by way of illustration and not by way of limitation.

EXPERIMENTAL

EXAMPLE 1

Preparation of thin slices

Soybean plants (Glycine max cv, Maple Arrow) are grown in a peatmoss, vermiculite and sand mixture (3:2:1 respectively) in the greenhouse at temperatures ranging from 13° C.–33° C. Additional light (high pressure sodium, 150 μE sec$^{-1}$m$^{-2}$) is provided during short (<16 h light) winter days. The plants are watered twice a week with a half strength MS (Murashige and Skoog (1962)) salt solution.

The pods, harvested when the embryos are 4–7 mm long, are surface sterilized 20–40 min. in a 1% sodium hypochlorite solution and washed twice with sterile distilled water. The immature seeds are isolated and the part containing the embryo axis, the cotyledonary shoots and approximately 25% of the proximal end of the cotyledons are dissected and discarded. The remaining cotyledonary fragments maintained within the seed teguments are placed on CM 3/0 medium gelified with Phytagar (0.7%) in 10 cm diameter Petri dishes. Approximately 40–60 cotyledons are placed in each Petri dish.

After 18 h–24 h, the cotyledonary fragments are separated from the teguments. Thin slices are dissected from the adaxial side of each cotyledonary fragment. These slices, approximately 2–5 mm long and approximately 1–3 mm wide include the epidermis and 1 to 4 layers of subepidermal mesophyll cells. The thin layer explants are now ready for regeneration (See Example 2) of a plant or transformation (See Example 7) followed by generation of transgenic plant.

EXAMPLE 2

Regeneration of Spybean Plants from Thin Layer Explants

The thin slices prepared as described above, are embedded in about a 1 mm thick coat of gelified (0.7% Phytagar) CM 3/0 medium and placed on gelified (0.7% Phytagar) CM 1/0 medium in 10 cm. diameter Petri dishes. Approximately 40–60 embedded slices are placed in each Petri dish and incubated at 27°±2° with a 16 h photoperiod in 40 μE sec$^{-1}$m$^{-2}$ fluorescent light.

After 10–15 days culture, spherical and ovoid embryoids are visible only at the epidermal side of the thin slices. Usually more than 70% of the slices are embryogenic and produce, on average, 5 embryoids. During the following 4 weeks, the growing embryoids emerge from the gelified CM 3/0 medium and can be transferred separately, or attached to the cotyledonary mother tissue, to gelified (0.7% Phytagar) CM 1/0 medium under unchanged environmental culture conditions.

On average about 15% of the embryos germinate into plants. Germination occurs as early as 3 weeks and as late as 4 months after transfer to CM 1/0 medium. Most of the embryoids form roots on CM 1/0 medium. When the plantlets reached 4–5 cm. they were potted in peatmoss/vermiculite/sand mixture (3/2/1 respectively) and placed in growth chambers at 27° C. under constant photoperiod (16h, 310 μE sec$^{-1}$m$^{-2}$) and watered using half-strength MS medium twice a week.

All the plants recovered are capable of setting flowers and fruit.

EXAMPLE 4

Construction of β-glucuronidase (gus) Expression Cassette, pCGN7304.

This cassette contains the gus gene, a double CaMV 35S promoter and the mas 3' region. The starting materials are the pBI221 plasmid (available from Clontech Laboratories, Palo Alto, Calif.) which contains the gus gene and pCGN1052.

(a) Plasmid pCGN1052

The mas 3' region was removed as a SacI to HindIII fragment from pCGN14 (*Nature* (1985) 317:741-744) and inserted into pUC18 to produce pCGN93. Plasmid pCGN93 was digested with HindIII, blunted with DNA polymerase I, and an EcoRI linker inserted, giving pCGN1034. An EcoRV to NaeI fragment was removed from pCGN40 (*Nature* (1985) 317:741-744) and a XhoI linker was inserted giving pCGN1036. pCGN1036 was then digested with EcoRI and the mas 3' EcoRI fragment from pCGN1034 inserted giving pCGN1040. pCGN1040 was partially digested with SacI, blunted with T-DNA polymerase, and a XhoI linker inserted at the 3' end of the mas 3' region resulting in pCGN1047. The XhoI fragment from pCGN1047 carrying the mas 5'-mas 3' cassette was then inserted into the XhoI site of pCGN1007 creating pCGN1052.

(b) Plasmid pCGN7000

Plasmid pI221 was digested with BamHI and SstI and ligated to pCGN1052 cut with BamHI and SstI to form pCGN7000. Construction of pCGN7000 is shown in FIG. 1.

(c) Plasmid pCGN7300

Plasmid pCGN2113, which contains a double CaMV 35S promoter, was cut with HindIII and SalI, then blunted with mung bean nuclease. XhoI linkers were added to form pCGN7300.

Figure 2:
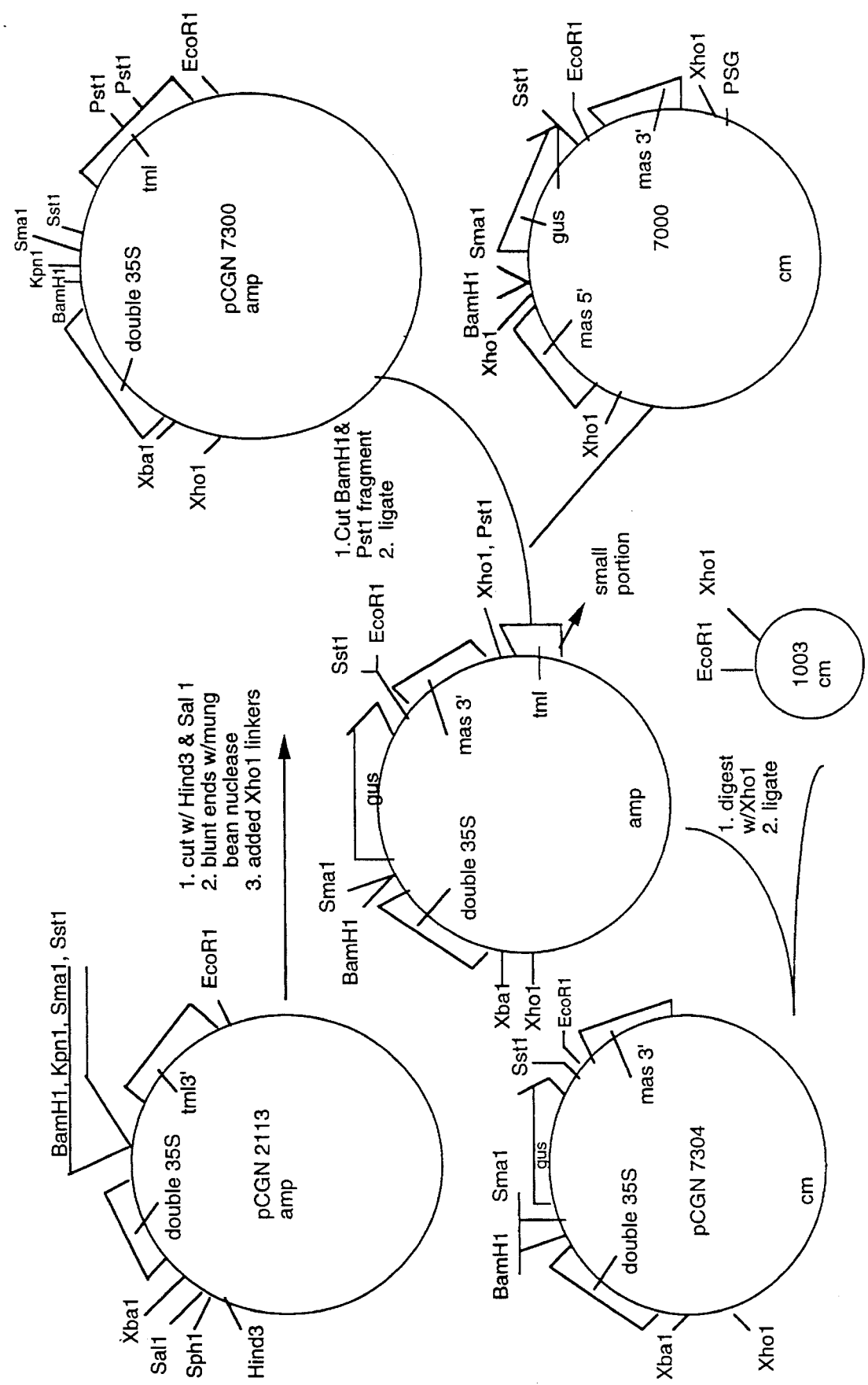
FIG. 2 shows the construction of the β-glucuronidase (gus) expression cassette, pCGN7304.

(d) Final Construction of Plasmid pCGN7304 pCGN7300 and pCGN7000 were cut with BamHI and PstI, then ligated. The resulting plasmid was then cut with XhoI and cloned into a chloramphenicol resistant background by digestion with EcoRI and BamHI and ligation to pCGN1003 to form pCGN7304. Construction of pCGN7304 is shown in FIG. 2.

EXAMPLE 4

Preparation of Bromoxcynil (Bxn) Expression Cassette, pBRX69

1. Construction of Plasmid

Plasmid pCGN986 contains a cauliflower mosaic virus 35S (CaMV 35S) promoter and a T-DNA tml 3'-region with multiple restriction sites between them.

(a) Shuttle Vector pCGN528

The shuttle vector used for this construct, pCGN528, was made as follows. pCGN525 was made by digesting a plasmid containing Tn5 which harbors a kanamycin gene (Jorgenson et. al., *Mol. Gen. Genet.* (1979) 177:65) with HindIII-BamHI and inserting the HindIII-BamHI fragment containing the kanamycin gene into the HindIII-BamHI sites in the tetracycline gene of pACYC184 (Chang and Cohen, *J. Bacteriol.* (1978) 134: 1141–1156). pCGN526 was made by inserting the BamHI fragment 19 of pTIA6 (Thomashow et. al., *Cell* (1980) 19:792–739), modified with XhoI linkers inserted into the SmaI site, into the BamHI site of pCGN525. pCGN528 was obtained by deleting the small XhoI fragment from pCGN526 by digesting with XhoI and religating.

(b) Plasmid pCGN206

Plasmid pCGN206 contains a CaMV 35S promoter and the CaMV region VI 3'-end The starting plasmids were pCGN148a and pMBKanXXI. pCGN148a containing a promoter region, selectable marker (KAN with 2 ATG's) and 3' region, was prepared by digesting pCGN528 with BglII and inserting the BamHI-BglII promoter fragment from pCGN147 (see below). This fragment was cloned into the BglII site of pCGN528 so that the BglII site was proximal to the kanamycin gene of pCGN528. pMB9KanXXI is a pUC4K variant (Vieira and Messing, *Gene* (1982) 19:259–268) which has the XhoI site missing but contains a functional kanamycin gene from Tn903. pCGN149a, made by cloning the BamHI-kanamycin gene fragment from pMB9KanXXI into the BamHI site of pCGN148a, was digested with HindIII and BamHI and ligated to pUC8 digested with HindIII and BamHI to produce pCGN169. This removed the Tn903 kanamycin marker. pCGN565 (a chloramphenicol resistant derivative of pUC18) and pCGN169 were both digested with HindIII and PstI and ligated to form pCGN203, a plasmid containing the CaMV 35S promoter and part of the 5'-end of the Tn5 kanamycin gene (up to PstI site, Jorgenson et al. (1979), supra). A 3'-regulatory region was added to pCGN203 from pCGN204, which includes an EcoRI fragment of CaMV (bp 408–6105) containing the region VI 3' region cloned into pUC18 (Gardner et al. (1981), supra). pCGN203 and pCGN204 were digested with HindIII and PstI and ligated to form pCGN206.

(c) pCGN147

The CaMV 35S promoter was cloned as an AluI fragment (bp 7144–7735) from CaMV (Gardner et al. *Nucl. Acids Res.* (1981) 9:2871–2888) into the HincII site of M13mp7 (Messing et al., Nucl. Acids Res. (1981) 9:309–321) to create C614. An EcoRI digest of C614 produced the EcoRI fragment from C614 containing the 35S promoter which was cloned into the EcoRI site of pUC8 (Vieira and Messing, *Gene* (1982) 19:259) to produce pCGN146. To trim the promoter region, the BglII site (bp 7670) of pCGN146 was treated with BglII and resected with pal31. Subsequently a BglII linker was attached to the Bal31 treated DNA to produce pCGN147. Construction of pCGN147 is described in U.S. application Ser. No. 188,361, filed Apr. 29, 1988, which disclosure is incorporated herein by reference.

(d) Final construction of pCGN986

The pTIA6 T-DNA tml 3'-sequences were subcloned from the Bam19 T-DNA fragment (Thomashow et al. (1980), supra) as a BamHI-EcoRI fragment (nucleotides 9062 to 12,823 —numbering as in Barker et al., *Plant Mol. Biol.* (1983) 2:335–250) and combined with the pACYC184 (Chang and Cohen (1978), supra) origin of replication as an EcoRI-HindIII fragment and a gentamycin resistance marker (from plasmid pLB41), obtained from D. Figurski) as a BamHI-HindIII fragment to produce pCGN417. The unique SmaI site of pCGN417 (nucleotide 11,207 of BamHI-SacI fragment was subcloned into pCGN565 to give pCGN971. The BamHI site of pCGN971 was changed to an EcoRI site using linkers. The resulting EcoRI-SacI fragment containing the tml 3' regulatory sequences was joined to pCGN975 which contains the Tn5 kanamycin resistance gene and the CaMV 35S promoter. The small part of the Tn5 gene was deleted from the 3'-end of the CaMV 35S promoter by digestion of pCGN975 with SalI and BglII, blunting of the ends and ligating to SalI linkers. The final expression cassette, pCGN986, contains the CaMV 35S promoter followed by two SalI sites, an XbaI site, BamHI, SmaI, KpnI and the tml 3' region (nucleotides 11207–9023 of the T-DNA).

2. Construction of pBRX43 pBRX43 contains a bxn gene excised from pBRX25 cloned into pCGN986 (described supra).

(a) Plasmid pBRX25

Construction of this plasmid is described in European application EPA 0 229 042 filed Jan. 7, 1987, which application is incorporated herein by reference. Briefly, the method was as follows. The nucleotide sequence of a 1212-bp Pst I-HincII DNA segment encoding the bromoxynil-specific nitrilase contains 65-bp of 5' untranslated nucleotides. To facilitate removal of a portion of these excess nucleotides, plasmid pBRX9 was digested with PstI, and treated with nuclease Bal31. BamHI linkers were added to the resulting ends. BamHI-HincII fragments containing a functional bxn gene were cloned into the BamH1-SmaI sites of pCGN565 (a pUC18 derivative containing a chloramphenicol resistance marker). The resulting plasmid, pBRX25, contains only 11 bp of 5' untranslated bacterial sequence.

(b) Final construction of pBRX43

A BamH1-SacI DNA fragment containing the bxn gene was excised from pBRX25 and cloned into the BamH1-SacI sites of pCGN986 to create plasmid pBRX43. The DNA from pCGN986 provides the necessary initiation and termination signals for expression of the chimeric mRNA in plants.

Figure 3:
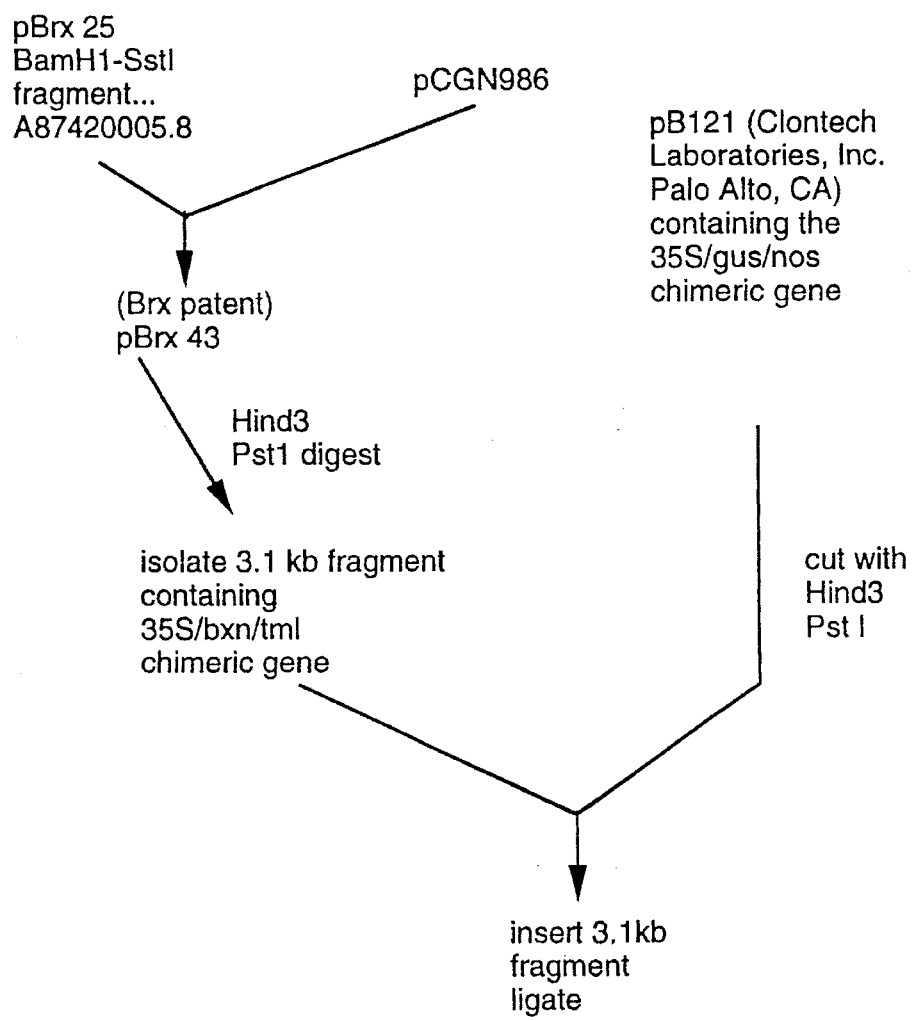
FIG. 3 shows the construction of the Bromoxynil (Bxn) resistance expression cassette, pBRX69.
Figure 3:
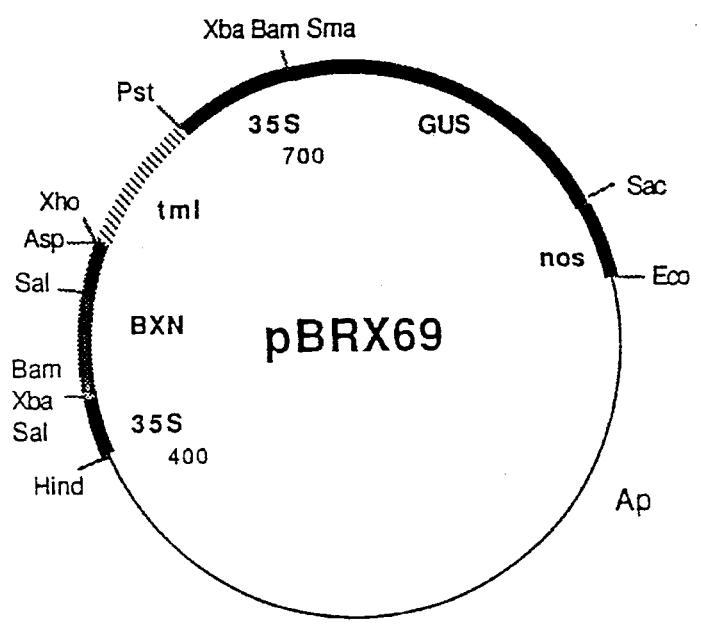

3. Construction of PBRX69 pBRX43 (supra) was digested with HindIII and PStI and a 3.1 kb fragment containing the 35S/bxn/tml chimeric gene isolated. This fragment was ligated to pBI221 (available from Clontech Laboratories, Palo Alto, Calif.) cut with HindIII and PstI, forming pBRX69. Construction of pBRX69 is shown in FIG. 3.

EXAMPLE 5

Adsorption of Expression Cassettes to Tungsten Particles

Expression cassettes prepared as described above are adsorbed to tungsten particles according to the following method. A stock tungsten suspension is prepared by adding 1 g of particles (average diameter 1.2 μm) to 20 ml absolute ethanol. The stock suspension is stored at −20° C. until use. Immediately prior to use, the stock suspension is diluted to 0.05 g/ml in absolute ethanol. An 0.5 ml aliquot of the tungsten suspension is centrifuged in a microfuge, the ethanol is decanted and the particles resuspended in 0.5ml distilled water. The washing step is repeated once and the particles then sterilized by autoclaving.

The particles are distributed into microfuge tubes, 25 μl/tube. DNA, 2.5 μg, is added to each tube. The DNA solution is 1 μg/μl DNA in water. Twenty-five microliters calcium chloride 2.5M is added to each tube followed by 2.5 μl of an 0.1M solution of spermadine (freebase) The suspension is incubated for 10 minutes at room temperature at which time the supernatant is decanted. The particles, with adsorbed DNA expression cassettes, are ready for use.

EXAMPLE 6

Preparation of Transgenic Soybean Plants

A. Transformation of Soybean Cells

Thin slices (prepared as described in Example 1) are placed approximately 7–9 cm from the stopping plate of a particle gun and bombarded from 1–3 times, according to the manufacturer's instructions. The particle gun is supplied by Bolistics, Geneva, N.Y.

B. Generation of Transgenic Soybean Plants

The transformed thin slices are embedded in about a 1 mm thick coat of gelified (0.7% Phytagar) CM 3/0 medium and placed on gelified (0.7% Phytagar) CM 1/1 medium containing 0, 20, 40, 60 or 80 mg/l of kanamycin or 0, $5\times10^{-6}$, $10^{-5}$ or $10^{-4}$M bromoxynil (Bxn) in 10 cm. diameter Petri dishes. The composition of the medium is shown in Table 1.

TABLE 1[1]

| Regeneration Medium | | | | | |
|---|---|---|---|---|---|
| Inorganics | | | | | |
| | mg/liter | mM | | mg/liter | μM |
| $NH_4NO_3$ | 1,000.0 | 12.5 | $H_3B_4$. | 5.0 | 82.0 |
| $KNO_2$ | 2,100.0 | 20.8 | KI | 1.0 | 6.0 |
| $KH_2PO_4$ | 325.0 | 2.4 | $MnSO_4H_2O$ | 15.0 | 90.0 |
| $NaH_2PO_4H_2O$ | 85.0 | 0.6 | $ZnSO_47H_2O$ | 5.0 | 17.5 |
| $CaCl_22H_2O$ | 600.0 | 4.1 | $CuSO_4.5H_2O$ | 0.1 | 0.4 |
| $MgSO_47H_2O$ | 435.0 | 1.8 | $Na_2MoO_4.2H_2O$ | 0.4 | 1.7 |
| $FeSO_47H_2O$ (EDTA) | 25.0 | 0.09 | $CoCl.6H_2O$ | 0.1 | 0.4 |

| Organics | | |
|---|---|---|
| | mg/liter | |
| Thiamine.HCl | 60 | 180 μM |
| Pyridoxine.HCl | 15 | 62.5 μM |
| Myo-inositol | 7500 | 219 mM |
| Sucrose | 26000.0 | 7.3M |
| Growth Regulators | | |
| Picloram | 0.06 | 0.26 μM |
| 6-Benzylaminopurine | 0.10 | 0.50 μM |

[1]Adjust pH to 6.8; add agar; autoclave for 15 min at 15 p.s.i. (120° C.).

Approximately 40–60 embedded slices are placed in each Petri dish and incubated at 27°±2° C. with a 16 h photoperiod 40 μE sec$^{-1}$m$^{-2}$ fluorescent light. After 10–15 days culture, spherical and ovoid embryoids are visible only at the epidermal side of the thin slices.

During the following 4 weeks, the growing embryoids emerge from the gelified CM 3/0 medium and can be transferred separately, or attached to the cotyledonary mother tissued, to gelified (0.7% Phytagar) CM 1/0 medium having the same concentrations of kanamycin or Bxn as in the initial selection medium. Data from these trials are provided in Tables 2 and 3 (see below). The environmental culture conditions are unchanged. environmental culture conditions are unchanged.

TABLE 2

Embryongenesis in thin slices bombarded with pBRX43 and exposed to Kanamycin (after 7 weeks of culture)

| | % of slices producing embryos | |
|---|---|---|
| Kan. conc. (mg/ml) | GUS (pCGN7304) | GUS + NPTII (pCGN7304 + pCGN778) |
| 0 | 31 ± 10 | 37 ± 22 |
| 20 | 7 ± 3 | 16 ± 6 |
| 40 | 2 ± 2 | 17 ± 7 |
| 60 | 0 ± 0 | 12 ± 5 |
| 80 | 0 ± 0 | 6 ± 2 |

TABLE 3

Embryogenesis in presence of Bromoxynil (Bxn) after 4 weeks of culture

| | % slices producing embryos | | |
|---|---|---|---|
| Bxn. conc.(M) | Non Bombarded | GUS (pCGN7304) | Bxn (pBRX69) |
| 0 | 51 | 31 | 30 |
| $5 \times 10^{-6}$ | 28 | 9 | 10 |
| $10^{-5}$ | 0 | 0 | 3 |
| $10^{-4}$ | 0 | 0 | 0 |

What is claimed is:

1. A method for genetically modifying a soybean plant cell capable of proliferation, said method comprising:

bombarding said plant cell with nucleic acid capable of replication in said plant cell, said nucleic acid having been absorbed to a bombardment particle, to produce a stably transformed leguminous plant cell; and growing said transformed cell in a nutrient medium whereby said nucleic acid is replicated, wherein said cell is comprised in an immature cotyledonary fragment, and wherein said fragment lacks the cotyledon embryo axis.

2. The method according to claim 1, wherein said nucleic acid is an expression cassette comprising in the 5' to 3' direction of transcription a promoter functional in said plant cell; a structural gene of interest, and a termination region functional in said plant cell.

3. The method according to claim 1, wherein said bombardment particle is a tungsten particle.

4. The method according to claim 1, wherein said cotyledonary fragment is a thin layer explant.

5. The method according to claim 4, wherein said explant is from about 2 to 4 mm long; from about 1 to 3 mm wide; and includes the epidermis and from about 1 to 4 layers of subepidermal mesophyll cells.

6. A method for genetically modifying a soybean plant cell capable of proliferation, said method comprising:

bombarding said plant cell with nucleic acid capable of replication in said plant cell, said nucleic acid having been absorbed to a bombardment particle, to produce a stably transformed leguminous plant cell; and growing said transformed cell in a nutrient medium whereby said nucleic acid is replicated, wherein said cell is comprised in a primary meristem fragment, and wherein said primary meristem fragment is a thin layer explant.

* * * * *